United States Patent
Rosenberg

[11] Patent Number: 5,158,976
[45] Date of Patent: Oct. 27, 1992

[54] CONTROLLING GLUTAMINE/GLUTAMATE RELATED NEURONAL INJURY

[75] Inventor: Paul A. Rosenberg, Newton, Mass.

[73] Assignee: The Children's Medical Center Corporation, Boston, Mass.

[21] Appl. No.: 605,528

[22] Filed: Oct. 29, 1990

[51] Int. Cl.$^5$ .................................. A61K 31/195
[52] U.S. Cl. .................................. 514/561
[58] Field of Search .................................. 514/561

[56] References Cited

PUBLICATIONS

Rosenberg GLIA 4:91–100 (1991).
Goldberg et al., Neuroscience Letters 94:52–57, 1988.
Hahn et al., 1988, Proc. Natl. Acad. Sci. U.S.A. 85:6556.
Rothman, 1983, Science 220:536.
Simon et al., 1984, Science 226:850.
Yamada et al., 1989, Brain Res. 498:351.
Barbour et al., 1988, Nature 335:433.
Bradford et al., 1976, Brain Res. 110:115.
Bradford et al., 1978, J. Neurochem. 30:1453.
Davies et al., 1989, Nature 338:500.
Garthwaite et al., 1986, Neuroscience 17:755.
Goldberg et al., 1988, Neurosci. Lett. 94:52.
Hamberger et al., 1979, Brain Res. 168:513.
O'Brien et al., 1986, J. Neurosci. 6:3290.
Rothman et al., 1987, Neuroscience 22:471.
Schousbee, 1981, Int. Rev. Neurobiol. 22:1.
Simantov, 1989, J. Neurochem. 52:1694.
Yamada et al., 1989, J. Neurosci. 9:3230.
Olney et al., 1986, Neurosci. Lett. 68:29.
Finkbeiner et al., 1988, Proc. Natl. Acad. Sci. U.S.A. 85:4071.
Choi et al., 1988, J. Neurosci. 8:185.
Choi, 1988, Neuron 1:623.
Bradford et al., 1989, Brain Res. 476:29.
Murphy et al., 1988, Br. J. Pharmacol. 95:932.
Honore et al., 1988, Science 241:701.
Rothman, 1984, J. Neurosci. 4:1884.
Beneveniste et al., 1984, J. Neurochem. 43:1369.
Choi, 1985, Neurosci. Lett. 58:293.
Choi et al., 1987, J. Neurosci. 7:357.
Davies et al., 1981, Neurosci. Lett. 21:77.
Lehmann et al. 1983, J. Neurochem. 40:1314.
Olverman et al., 1984, Nature 307:460.
Rosenberg et al., 1989, J. Neurosci. 9:2654.
Kvamme et al., 1985, Meth. Enzymol. 113:231.
Rosenberg et al., 1989, Neurosci. Lett. 103:162.
Pearce et al., 1987, FEBS Letts. 223:143.
Weiloch, 1985, Science 230:681.
Aharony et al., 1984, Life Sciences 35:2135.
Shapiro et al., 1979, J. Bio. Chem. 254:2835–2838.

*Primary Examiner*—S. J. Friedman

[57] ABSTRACT

A method of inhibiting neuronal injury or death in a human patient comprising administering an inhibitor of enzymatic conversion of glutamine to glutamate in an amount sufficient to inhibit the conversion of glutamine to glutamate.

2 Claims, No Drawings

CONTROLLING GLUTAMINE/GLUTAMATE RELATED NEURONAL INJURY

BACKGROUND OF THE INVENTION

This invention was made in the course of work under a grant or award from the U.S. government; therefore, the U.S. government has rights in the invention.

The invention is in the general field of treating conditions involving neuronal injury or death.

A variety of conditions in the mammalian central nervous system, including trauma, anoxia, ischemia, hypoglycemia, seizures, and several neurodegenerative diseases can result in neuronal injury and death. Glutamate, a factor in such injury and death is thought to be a major excitatory neurotransmitter and acts through at least three major receptor subtypes, classified on the basis of their agonists as quisqualate, kainate, and N-methyl-D-aspartate (NMDA) receptors. Activation of the NMDA receptor, for example, results in the opening of channels that allow $Ca^+$ influx. Excessive stimulation of the NMDA receptor has been implicated in the pathophysiology of neuronal death (Pearce et al., 1987, FEBS Letters 223:143)). Wieloch (1981)*Science* 230:681-683 report that NMDA receptor activation induced hypoglycemic neuronal damage, and that NMDA receptor antagonists prevented this effect; an example of one such antagonist is 2-amino-5-phosphonovalerate (APV) (*Davies* et al. (1981) *Neurosci. Lett.* 21:77-81; (Olverman et al., Nature 307:460, 1984).

Rothman (1984) J. Neurosci. 4:1884-1891 report that DGG ($\gamma$-D-glutamylglycine), a postsynaptic blocker of excitatory amino acids, prevents the death of anoxic hippocampal neurons in vitro. Other reports [*Choi* (1985) *Neurosci. Lett.* 58:293-297; *Choi* (1987) *J. Neurosci.* 7:357- 368] conclude that glutamate is a potent and rapidly acting neurotoxin in cortical cell culture. Rosenberg et al. (1998) *Neurosci. Lett.* 103:162 168 report that astrocyte-poor neuronal cultures are 100-fold more vulnerable to glutamate toxicity than astrocyte-rich cultures.

SUMMARY OF THE INVENTION

The invention features a method of inhibiting neuronal injury or death in a human patient which includes administering an inhibitor of the enzymatic conversion of glutamine to glutamate in an amount sufficient to inhibit this enzymatic conversion. I use the phrase "enzymatic conversion" to mean conversion of neuronal glutamine to glutamate through one or more enzyme-catalyzed reactions.

Preferred therapies according to the invention involve inhibition of the enzyme glutaminase (E.C. 3.5.1.2) particularly neuronal glutaminase. The invention is generally useful to treat patients affected by a disease or disorder in which neuronal injury or death is related, directly or indirectly, to glutamate toxicity; e.g., the disease or disorder may be stroke, hypolycemia, trauma, epilepsy, amyotrophic lateral sclerosis, hypoxia, ischemia. The invention may also be useful to treat other neurological disorders such as Parkinson's or Alzheimer's diseases.

Preferred inhibitors of enzymatic conversion of glutamine to glutamate are: diazo-oxo-norleucine, azaserine, acivicin, azotomycin, albizzin, and alpha-amino-adipic acid (all from Sigma Chemical Corp., St. Louis, Mo.); amino-chloro-oxo-pentanoic acid; and o-carbamoyl-L-serine (Shapiro et al., 1979, J. Biol. Chem. 254:2835), D,L-gammaglutamyl(o-carboxy)-phenylhydrazide and serine-borate complex (both, Aharony et al., Life Sciences, 1984, 35:2135). In general, the inhibitor may be administered in combination with a glutamate antagonist, e.g., MK801 (dizcilpine, Research Biochemicals, Inc.), NBQX (2,3 dihydroxy 6-nitro-7-sulfamoyl-benzy-(F-quinoxalin) (Ferrosan,Denmark), APV (aminophosphonovaleric acid), CPP (3-(-carboxypiperizin-4-yl)-propyl-1-phosphonic acid)), or dextramethorphan, (APV, CPP and dextra-methorphan can be obtained from Tocras Neuramin, Essex, England). (Of the above-identified inhibitors, diazo-oxo-norleucine, azaserine, amino-chloro-oxo-pentanoic acid, D,L-gammaglutamyl(o-carboxy)-phenylhydrazide, and azotomycin are thought to be irreversible inhibitors.)

As explained below, to ameliorate the effect of the inhibitor on peripheral tissue when the inhibitor is administered systemically, it is desirable to co-administer glutamine or a second inhibitor of glutaminase, which is incapable of crossing the blood/brain barrier and which is reversible in its inhibitory effects on the enzymatic conversion (at least in peripheral tissues). The glutamine or the second inhibitor are provided in an amount sufficient to interact with glutamine conversion enzyme in peripheral tissue, reducing irreversible, binding by the primary inhibitor. "Systemic" administration means administration to a patient by a route other than the central nervous system, as described in the Use section, below. Glutamine is preferred because it can cause transient inhibition of enzymatic conversion of glutamine to glutamate in peripheral tissues, but not in the central nervous system, since glutamine does not cross the blood/brain barrier. Alternatively, a reversible inhibitor may be used to block the activity of glutaminase in peripheral tissues.

The invention also features a method of screening for an inhibitor of neuronal injury or death in a mammal (preferably a human patient), which includes providing a neuronal culture, incubating the culture in the presence of glutamine in combination with a potential inhibitor of enzymatic conversion of glutamine to glutamate, for a time and under culture conditions adequate to expose the neurons to glutamine and the potential inhibitor, and determining the inhibitory effect if any on that enzymatic conversion. For example, such a determination can be made by determining either cellular survival in the culture, or the appearance of glutamate in the extracellular medium.

In the above screening method, as outlined below, the culture may be either astrocyte-poor or astrocyte-rich. The inhibitors to be screened include: diazo-oxonorleucine, azaserine, acivicin, amino-chloro-oxo-pentanoic acid, alpha-amino-adipic acid, azotomycin, o-carbamoyl-L-serine, D,L-gamma-glutamyl(o-carboxy)-phenylhydrazide, serine-borate complex, and albizzin.

While not wishing to bind myself to any specific theory, the importance of the invention may derive at least in large part from its ability to interrupt a natural mechanism in which an initial neuronal insult (e.g. the presence of extraneuronal glutamate) instigates a positive feed-back loop, generating evermore glutamate in catalytic fashion. This feedback loop is explained in greater detail below. In essence, the invention interrupts the loop at its catalytic center, providing a potent control on events that otherwise result in a cascade of neuronal injury and death. Because control is exercised in catalytic fashion, it is necessary to use only enzyme-inhibiting quantities of the therapeutics.

Other features and advantages of the invention will be apparent from the following description of the preferred embodiments thereof, and from the claims.

DESCRIPTION OF THE PREFERRED EMBODIMENT

The method of inhibiting neuronal death in a patient by administering an inhibitor of the enzymatic conversion of glutamine to glutamate is based on the use of inhibitors of the enzymatic conversion, administered as described below in the "Use" section. The scope and importance of the invention can be appreciated in view of the observations that: (a) exposure of astrocyte-poor cultures to fresh medium containing 10 μM glutamate and 2 mM glutamine results in the accumulation of substantial quantities of glutamate coincident with the death of neurons in the cultures; (b) neuronal death in these cultures produced by exposure to 10 μM glutamate is not sufficient to raise the extracellular concentration of glutamate, in the absence of extracellular glutamine; and (c) extracellular glutamate which accumulates following glutamate-induced injury to astrocyte-poor cultures is shown to be derived from extracellular glutamine.

It appears that the extracellular glutamate observed in the presence of glutamine is not simply glutamate released from pre-existing intracellular stores from dead or dying cells, but rather generated from a positive feedback control loop within the cerebral cortex which generates extracellular glutamate, thus contributing to neuronal destruction.

The loop begins with an insult to neurons sufficient to trigger neuronal injury or death, such that the integrity of neurons is disrupted. Such events include glutamate toxicity, but any injury which allows abnormal access of intracellular enzymes to extracellular glutamine can trigger the loop. Specifically, the loop can be triggered either by release from injured neurons of one or more intracellular enzymes including those capable of hydrolyzing glutamine to glutamate or by abnormal access of extracellular glutamine to the intracellular enzymes through, e.g., leaky membranes. These enzymes then convert glutamine to glutamate. The loop is therefore fueled by glutamine, which is present extracellularly in large amounts in the cerebrospinal fluid (Fishman (1980)*Cerebrospinal Fluid in Disease of the Nervous System*, Saunders, Philadelphia, pp. 234) and in hippocampal extracellular fluid (Lehman et al. 1983), *J. Neurochem.* 40:1314–1320; Benveniste et al., (1984) *Neurochem.* 43:1369–1374;). As additional neurons are injured by the resulting extracellular glutamate, additional intracellular enzymes are exposed to extracellular glutamine, producing glutamate.

Having described the positive feed-back loop responsible for neuronal injury, those skilled in the art will appreciate that enzyme inhibitors useful in the invention, are those which inhibit conversion of glutamine to glutamate. The most common known conversion path involves glutaminase (E.C.3.5.1.2), but other enzymatic conversions are within the scope of the invention.

Inhibitors to be evaluated for use in the invention according to the protocols described below include, but are not limited to, diazo-oxo-norleucine, azaserine, acivicin, amino-chloro-oxo-pentanoic acid, alpha-amino-adipic acid, azotomycin, o-carbamoyl-L-serine, D,L-gamma-glutamyl(o-carboxy)-phenylhydrazide, serine-borate complex, and albizzin.

Candidate inhibitors may be tested prior to administration to a patient in the in vitro screening method described below in the Examples. Potential inhibitors are first tested for a lack of neuronal or glial toxicity. Once drugs possessing in vitro inhibitory activity and lacking neuronal toxicity are identified, they may be administered according to the invention to a patient exhibiting symptoms of a disease or disorder associated with neuronal injury or death, particularly to patients in which neuronal injury or death is a result of glutamate toxicity. Preferred inhibitors are those which are capable of crossing the blood/brain barrier.

It is possible to test directly for the desired inhibition of enzymatic activity. For example, glutaminase inhibition may be tested directly as described in Example 2.

EXAMPLE 1

Screening of potential inhibitors

The toxicity testing and screening procedure detects glutamine conversion to glutamate resulting in neuronal death, and involves exposing an astrocyte-rich or -poor culture to the drug, under conditions described below, and determining neuronal viability in the culture, as follows. Astrocyte-rich and astrocyte-poor cultures may both be tested according to the invention. The relative advantages of testing both types of cultures are explained below.

Astrocyte-rich cultures may more closely mimic the environment of the brain, the environment in which therapy occurs, compared to a culture having fewer astrocytes. On the other hand, drug effectiveness on an astrocyte-poor culture provides information as to the toxicity of drugs which do not have access to neuronal processes surrounded by astrocytes, as is the case in astrocyte-rich cultures.

Where astrocyte-rich cultures are tested, neuronal injury is induced by oxygen or glucose deprivation. Neuronal injury in astrocyte-poor cultures can be induced by oxygen or glucose deprivation or by exposure to toxic concentrations of glutamate, or by oxygen or glucose deprivation of cultures grown in glutamine that is not contaminated by glutamate. A medium containing a low concentration of glutamate can be obtained by incubating astrocyte-poor cultures in culture medium for about 12 days or less. Since neurons are only sensitive to glutamate after about 12 days in culture, endogenous glutamate is taken up by the 12th day and neurons will thus survive if the last culture change is prior to the 12th day of culture despite the presence of glutamine. The culture can then be subject to oxygen or glucose deprivation or exposure to exogenous glutamate agonists.

Neuronal cultures are derived from embryonic (fetal day 16) Sprague-Dawley rat cerebral cortex, are prepared as described in Rosenberg and Aizenman, (1989, Neuroscience Letters 103:162) and Rosenberg and Dichter (1989, Journal of Neuroscience 9:2654). Following dissociation in 0.027% trypsin, cells are plated on poly-L-lysine (astrocyte-poor) or collagen and poly-L-lysine (astrocyte-rich) coated glass coverslips in Dulbecco's modified Eagle's medium (DME)/Ham's F-12/heat inactivated iron supplemented calf serum (HyClone) 8:1:1 (DHS). Astrocyte-poor cultures are produced by exposure to 5 μM cytosine arabinoside for 48 hours, beginning at 4 days in vitro. After inhibition, medium is replaced with DME/Eagle's Minimal Essential Medium (MEM)/F12 (4:5:1) with the N2 supplements of Bottenstein and Sato (*Bottenstein,* 1983), catalase 1 μg/ml (*Walicke* et al., 1986). Glutamine (Gibco) is added to a final concentration (exclusive of serum) of 2 mM. Medium is not subsequently replaced because regular medium change is associated with diminished survival of neurons. Glucose is measured from 12 days to 5 weeks in vitro in the astrocyte-poor cultures and is found to have approximately halved during this period (to 5–6 mM). To help prevent evaporation, dishes are placed on pads of water-soaked filter paper in 60 mm petri dishes. Cultures are incubated at 35° C. in 5% $CO_2$/95% air. Cultures treated in this way survive up to 6 weeks in vitro. They are used for experiments at 3–5 weeks in vitro.

The conventional astrocyte-rich culture system described herein is commonly referred to as cerebral cortex in dissociated cell culture (*Dichter,* 1978). These cultures are exposed to cytosine arabinoside for 24–72 hours, after the glial layer had become confluent and, subsequently, media is changed three times per week with DHS.

Immunocytochemistry using tetanus toxin/anti-tetanus antibody demonstrated that 40% of total cells present are tetanus positive (*Rosenberg and Aizenman,* 1989) in astrocyte-poor cultures. However, because of the dense mat of neuronal processes immediately adjacent to most soma, and which is strongly tetanus positive, in order to make a positive identification of tetanus positive soma it is necessary to detect staining at the vertex of the soma. This requirement would be expected to result in an underestimate of the number of neurons in astrocyte-poor cultures based on tetanus immunochemistry. It has been found that 32±20% of total cells are glial fibrillary acidic protein (GFAP) and vimentin positive, suggesting that approximately 70% of total cells present in an astrocyte-poor culture are neurons (for methods, see Rosenberg and Dichter, 1987/1988). Cells in a culture may also be morphologically identified using phase contrast optics; approximately 69±21% of cells present in an astrocyte-poor culture are neurons. Electrophysiological experiments in which morphological identification of cells is used to choose cells for intracellular and patch-clamp recording confirm the reliability of morphological identification (*Rosenberg, Schweitzer, and Dichter,* 1985; *Rosenberg and Aizenman,* 1989). Total cells are counted using bisbenzamide (Hoechst 33258) as a fluorescent nuclear stain (Bruner and Bursztajn, 1986). For this purpose, bisbenzamide is added to the mounting medium (glycerol plus n-propyl gallate; Giloh and Sedat, 1982) at a concentration of 5 μg/ml, and cultures may be examined using epifluorescence microscopy with a 365 nm broad pass excitor filter, 395 nm dichroic mirror, and a 420 nm long pass barrier filter.

Approximately 5000 GFAP positive cells (astrocytes) are present per astrocyte-poor coverslip culture. Anti-GFAP and anti-vimentin immunochemistry revealed that non-neuronal cells in astrocyte-rich cultures are >90% astrocytes (Rosenberg and Dichter, 1987). Tetanus immunochemistry in astrocyte-rich cultures revealed that 6% of total cells present ($1.4 \times 10^5$ cells) are neurons (Rosenberg and Aizenman, 1989). Therefore, there are approximately 26 times $\{[1.4 \times 10^5 - (6\% \times 1.4 \times 10^5)]/5 \times 10^3\}$ the number of astrocytes in astrocyte-rich cultures as in astrocyte-poor cultures.

Both astrocyte-rich and astrocyte-poor cultures are maintained in culture for at least 12 days prior to toxicity testing. The toxicity of potentially useful drugs may then be tested as follows. Toxicity experiments are performed using astrocyte-poor cultures at 12 days to 5 weeks in vitro, and, using astrocyte-rich cultures, from 12 days to 6 months in vitro. Cultures are washed once with physiological saline (in mM:NaCl, 145; KCl, 3; $CaCl_2$, 1.8; $MgCl_2$, 1.0; glucose, 8; $NaH_2PO_4$, 2.4; $NaH_2PO_4$, 0.42), 2 ml/35 mm dish containing 5 coverslips, then placed in wells with 0.5 ml MEM (without glutamine; Sigma) per well. Wells are incubated with agitation 70 minutes at 37° C., and then coverslip cultures (astrocyte-poor at 21 days in vitro) are added and returned to the incubator.

For determination of toxicity, the inhibitor of conversion of glutamane to glutamate is added at different concentrations to the media.

After a selected interval, e.g., 1–24 hours, the toxicity testing is terminated by replacing medium with fixative (2.5% glutaraldehyde in physiological saline), and the culture is counted while still in fixative, at 125×. Ten successive fields along a diameter are counted per coverslip, depending on the culture density, representing 10% of the total area of the coverslip. The number of fields counted are the same for all coverslips in a given experiment. Neurons are identified as isolated non-granular phase bright cells 10 to 30 μm in diameter, often with a pyramidal or bipolar morphology; only these cells are tetanus-positive. Approximately 1500 to 10,000 neurons are present per astrocyte-poor coverslip.

For purposes of identifying potential glutamine to glutamate convertion inhibitors for administration to patients to inhibit neuronal death, a level of toxicity that is acceptable is one which gives no significant neuronal or glial death at a concentration sufficient to inhibit the enzyme responsible for conversion of glutamine to glutamate. It is useful to test the potential toxicity of putative inhibitors in astrocyte-rich cultures and in astrocyte cultures. In astrocyte-poor, astrocyte-rich, and astrocyte cultures, the toxicity of the agents against neurons as well as astrocytes will be assessed by one or more criteria, e.g., cell counts, morphological appearance of cells, and/or the release from the cells of one or more intracellular enzymes, e.g., LDH ??.

Glutamine can be obtained from Sigma Chemical Company (St. Louis, Mo.) and Gibco (Grand Island Biological Co., N.Y.). Thin layer chromatography supplies are obtained from Sigma. Radiochemicals are obtained from Amersham. Rats are obtained from Charles River Laboratories.

EXAMPLE 2

Direct Testing for Glutaminase Inhibition

In order to test directly for the ability of a drug to inhibit the enzymatic conversion of glutamine to glutamine, an in vitro assay may be performed in which the conversion of glutamine to glutamate by the enzyme(s), e.g., glutaminase, is inhibited.

An in vitro cell-free enzymatic inhibition assay may be performed by any conventional procedure, e.g., see *Kvamme* et al., 1985, *Methods in Enzymology* 113:241. For example, glutaminase may be tested in this assay.

A potentially useful drug may also be tested for inhibition of glutamine to glutamate conversion under culture conditions. Astrocyte-poor cultures are washed and placed in fresh medium (MEM or Earle's Salt Solution) containing 2 mM glutamine at selected intervals; the medium is sampled and assayed for glutamate using HPLC.

The presence of glutamate and glutamine in culture medium after exposure to astrocyte-poor cultures can be determined using HPLC with ninhydrin detection. Amino acid analysis is performed on a Beckman 7300 Amino Acid Analyzer. Samples are quickly frozen and stored at −20°. At the time of assay they are thawed and deproteinized with 2% (final concentration) sulfosalicylic acid. A 20 cm cation exchange column (Beckman #338075) is used with operating pressure of 1000-1500 psi and Beckman buffers. Glutamic acid and glutamine elute between 12-25 minutes during flow-through of the first running buffer. Detection is by ninhydrin. An internal standard, S-2-aminoethyl-L-cysteine, is run with each sample.

Alternatively, $^{14}$C-glutamine is present, and at selected times, medium is sampled and assayed by thin-layer chromatography for $^{14}$C-glutamate. The effect of adding potential inhibitors on the appearance of glutamate or on the conversion of $^{14}$C-glutamine to $^{14}$C-glutamate will be determined.

After an 18-24 hour incubation, glutamate is detected using this assay at concentrations as high as 595 μM. Extracellular glutamate concentration is detectable to a lower limit of detection n=10 μM. Assays can be performed on fresh medium, medium incubated with astrocyte-poor cultures, or medium incubated without cultures to compare the differences in glutamine or glutamate content.

ANIMAL TESTING

The above-identified inhibitors and also drugs identified in vitro according to the invention as potential in vivo inhibitors of glutamine to glutamate conversion can be tested in animals for their effectiveness in inhibiting or preventing neuronal injury and/or death.

Conventional animal testing systems are well-known in the art. Each animal may be injected with a range of doses of the drug and the toxicity or lack of toxicity of the drug may be assessed by the survival rate of the animals. Animals which exhibit symptoms of neuronal injury, or animals subject to conditions generating cerebral infarction (i.e., stroke), e.g, oxygen or glucose deprived animals, can then be tested. The effects of the drug on peripheral tissues can be assessed by histological examination of the tissues. Based on these in vivo tests, the overall effectiveness of the drug can be determined, and an effective dose and mode of administration can also be determined.

MECHANISM OF ACTION

At least three types of mechanisms may be envisioned in which cell injury and, in particular, neuronal injury, may be coupled with extracellular glutamate accumulation: (1) cell injury permits uncontrolled access of medium glutamine to enzymatic conversion of glutamine to glutamate still localized within cells; (2) cell injury causes the release of the glutamine to glutamate converting enzyme into the extracellular medium; and (3) cell injury may potentiate vesicular release of glutamate, e.g., by elevation of intracellular $Ca^+$. In all three of the above mechanisms, inhibitors of the enzymatic conversion of glutamine to glutamate can be expected to control neuronal injury and/or death which occurs through one or more of the mechanism.

USE

The invention method of screening drugs for inhibitors of glutamine converting enzymatic activity may be used to identify drugs which may be useful in treating disease involving neuronal death. The drugs may then be administered according to the invention, alone or in combination with glutamate antagonists or other drugs, e.g., $Ca^+$ antagonists, which affect glutamate release from neurons and astrocytes, to treat neuronal death resulting from stroke, head trauma, intracerebral hemorrhage, perinatal asphyxia, hypoglycemia, and status epilepticus, and to treat such diseases as Parkinson's disease, Huntington's disease, and Alzheimer's disease.

Inhibitors may be administered by conventional routes of drug administration, e.g., orally, intravenously, intranasally, or intraperitoneally; or by spinal tap, in which the drug flows into the subarachnoid space; and in conventional amounts. Inhibitors that are incapable of crossing the blood-brain barrier and therefore do not have access to the central nervous system, may be modified chemically so as to become accessible through the blood-brain barrier. Inhibitors which can cross this barrier, e.g., those which are transported across membranes by specific transport systems, e.g., amino acid transport systems, or are lipid-soluble, and which are toxic in peripheral tissues may be administered in combination with high concentrations of glutamine (which does not cross the blood brain barrier), which competitively inhibits the interaction of the inhibitor with the glutamine converting enzyme in peripheral tissues.

I claim:

1. A method of reducing neuronal injury or death in a human patient comprising administering to said patient an inhibitor of enzymatic conversion of glutamine to glutamate in an amount to inhibit said enzymatic conversion, wherein said inhibitor is selected from the group consisting of diazo-oxo-norleuicine, azaserine and alpha-amino-adipic acid.

2. The method of claim 1 wherein said inhibitor is diazo-oxo-norleucine.

* * * * *